(12) United States Patent
Desforges et al.

(10) Patent No.: US 9,216,262 B2
(45) Date of Patent: Dec. 22, 2015

(54) DEVICE FOR DETECTING THE OBSERVANCE BY A PATIENT OF AN OXYGEN-THERAPY TREATMENT

(75) Inventors: Daniel Desforges, Paris (FR); Marie Jaillet, Juvisy sur Orge (FR); Joseph Pierquin, Molsheim (FR); Emilie Mouren, Paris (FR); Patrick Leger, Saint Didier Au Mont d'Or (FR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 708 days.

(21) Appl. No.: 12/937,527

(22) PCT Filed: Apr. 10, 2009

(86) PCT No.: PCT/FR2009/050648
§ 371 (c)(1),
(2), (4) Date: Oct. 12, 2010

(87) PCT Pub. No.: WO2009/136101
PCT Pub. Date: Nov. 12, 2009

(65) Prior Publication Data
US 2011/0034819 A1    Feb. 10, 2011

(30) Foreign Application Priority Data
Apr. 21, 2008 (FR) ..................... 08 52662

(51) Int. Cl.
*A61B 5/02* (2006.01)
*A61M 16/00* (2006.01)
(Continued)

(52) U.S. Cl.
CPC .............. *A61M 16/00* (2013.01); *A61B 5/0816* (2013.01); *A61M 16/0677* (2014.02);
(Continued)

(58) Field of Classification Search
CPC ...... A61B 5/097; A61B 5/083; A61B 5/0836; A61B 5/085; A61B 5/1135; A61B 5/113; A61B 5/0809; A61B 5/0878; A61B 5/087; A61B 5/09; A61B 5/0871; A61B 5/093; A61B 5/095; A61B 7/003; A61F 5/08; A61M 16/0488; A61M 16/00; A61M 16/0051; A61M 16/06; A61M 16/0666
USPC .................................................. 600/529–543
See application file for complete search history.

(56) References Cited

U.S. PATENT DOCUMENTS 5,522,382 A * 6/1996 Sullivan et al. .......... 128/204.23
5,603,315 A    2/1997 Sasso
(Continued)

FOREIGN PATENT DOCUMENTS

| DE | 296 22 321 | 3/1997 |
|---|---|---|
| FR | 2 916 291 | 11/2008 |
| GB | 2 178 193 | 2/1987 |
| WO | WO 96 09847 | 4/1996 |

(Continued)

OTHER PUBLICATIONS

International Search Report for PCT/FR2009/050648.

*Primary Examiner* — Patricia Mallari
*Assistant Examiner* — Vasuda Ramachandran
(74) *Attorney, Agent, or Firm* — Allen E. White

(57) ABSTRACT

The invention relates to a device for implementing a system for detecting the observance by a patient of an oxygen-therapy treatment involving an oxygen supply, and for recording the data of said treatment and transmitting said data. The invention also relates to the use of said device, and to a method for tracking the observance of an oxygen-therapy treatment.

6 Claims, 4 Drawing Sheets

(51) Int. Cl.
*A61B 5/08* (2006.01)
*A61M 16/06* (2006.01)
*A61M 16/10* (2006.01)
*A61B 5/00* (2006.01)

(52) U.S. Cl.
CPC ........... *A61M 16/101* (2014.02); *A61B 5/0022* (2013.01); *A61B 5/7257* (2013.01); *A61M 16/0051* (2013.01); *A61M 2016/0021* (2013.01); *A61M 2016/0027* (2013.01); *A61M 2202/0208* (2013.01); *A61M 2202/03* (2013.01); *A61M 2205/3592* (2013.01); *A61M 2205/52* (2013.01); *A61M 2205/8212* (2013.01)

(56) References Cited

U.S. PATENT DOCUMENTS

| | | |
|---|---|---|
| 5,706,801 A | 1/1998 | Remes et al. |
| 5,890,490 A | 4/1999 | Aylsworth et al. |
| 2002/0096174 A1* | 7/2002 | Hill et al. ................. 128/205.11 |
| 2004/0103899 A1* | 6/2004 | Noble ...................... 128/207.18 |
| 2007/0023039 A1 | 2/2007 | Ishizaki et al. |
| 2008/0177195 A1* | 7/2008 | Armitstead ................... 600/529 |

FOREIGN PATENT DOCUMENTS

| | | |
|---|---|---|
| WO | WO 98 18513 | 5/1998 |
| WO | WO 2005 067520 | 7/2005 |

* cited by examiner

DEVICE FOR DETECTING THE OBSERVANCE BY A PATIENT OF AN OXYGEN-THERAPY TREATMENT

This application is a 371 of International PCT Application PCT/FR2009/050648, filed Apr. 10, 2009, the entire contents of which are incorporated herein by reference.

FIELD OF THE INVENTION

The present invention pertains to a device allowing the detection, with regard to a patient, of the observance of an oxygen-therapy treatment with a continuous oxygen feed as well as to the use of this device. The invention also pertains to a method for tracking the observance of an oxygen-therapy treatment.

BACKGROUND

About 5 to 15% of adults from industrialized countries suffer from chronic obstructive bronchopneumopathy, termed "COBP".

The World Health Organization estimates that COBP is currently the fifth greatest cause of mortality in the world, and that by 2020, it will be the third greatest cause of mortality.

Oxygen-therapy is an effective treatment for patients suffering from respiratory insufficiencies, in particular COBP. Treatment, if it is properly followed, can lead to a sharp improvement in the patient's quality of life and reduce the number of exacerbations of the disease and therefore of hospitalizations.

However, the effects of oxygen-therapy are negligible, or indeed zero, if the patient does not observe his treatment, for example if the intake of oxygen occurs for a duration of less than 15 hours per day. Thus, in the study of these diseases and the care associated therewith, it is therefore essential to ascertain patients' observance, that is to say to measure the actual time during which they follow their treatment.

Numerous studies aimed at quantifying the impact of such and such a patient education program, at more precisely measuring the influence of oxygen-therapy on the duration and the quality of life of patients, or else at evaluating the medicoeconomic viability of home care, make it necessary to ascertain patients' observance.

Today, the data used for these studies are quite often qualitative data, arising directly from the gathering of information from patients, in the form of investigations or surveys, or in the best cases, of estimations of patients' oxygen consumption based on the number of cylinders consumed, the volume of liquid oxygen invoiced, the number of hours for which the oxygen concentrator is operating, etc.

It is therefore never actual data relating to the duration of treatment, to the patient's respiratory frequency and, consequently, to their state of health in general.

Moreover, the document U.S. Pat. No. 5,706,801 describes a device used to provide oxygen-enriched air, concentrated or compressed, to a patient via a diffuser. It comprises a detection and communication system having to be used in a periodic manner to verify the performance of the device and whether the oxygen provided to the patient corresponds to what was prescribed, that is to say whether the flow rate and the concentration of oxygen are in accordance with the doctor's instructions. However, this device does not make it possible to detect the presence of the patient and to recover information regarding his state of health.

Furthermore, the document US-A-2007/0023039 teaches an apparatus which makes it possible to enrich the patient's environment with oxygen, to detect the patient's respiration but not his respiratory frequency, and to verify whether he is observing his treatment. It comprises, between the oxygen source and the cannula, an ultrasound sensor which measures the speed of propagation of the sound waves and the flow rate of oxygen entering the cannula and, moreover, a component making it possible to synchronize or regulate the oxygen demand at the time of respiration. A frequency shift due to respiration is used to detect the patient's respiration (frequencies calculated on the basis of sound waves). However, at no time is the respiratory frequency measured.

Moreover, these systems exhibit the drawbacks of not being able to achieve the desired autonomy and of being voluminous.

There therefore exists a requirement for a device capable of alleviating these various drawbacks while making it possible to detect whether the patient is indeed following his prescribed treatment, of recording these data, of transmitting them locally and remotely so as to be able to alert the patient or the care center to which he is attached should the treatment not be followed, of being adaptable to any type of oxygen source, and of exhibiting very significant autonomy of at least one year.

SUMMARY OF THE INVENTION

The present invention provides a device for detecting the observance of an oxygen-therapy treatment with feeding of oxygen to a patient via a cannula delivering oxygen to the airways of the patient. This device allows the recording of the data of the treatment and the transmission of the data. The device comprises two sensors of absolute pressure, one for measuring the pressure in the cannula, the other for measuring the atmospheric pressure, or a differential pressure sensor, a micro-processor implementing an algorithm capable of transforming the pressure measurements into respiratory frequencies of the patient and of deducing therefrom the duration of the daily treatment, a memory chip making it possible to record these data, a radiofrequency antenna making it possible to ensure the wireless transmission of the data, and a battery allowing the system to operate in complete autonomy. The present invention also provides for the use of this device for tracking the observance of an oxygen-therapy treatment by measuring the duration of treatment of the patient and the patient's respiratory frequency. The present invention further provides a method for tracking the observance of an oxygen-therapy treatment by measuring the duration of treatment of the patient with the claimed device. This method involves the detection of an oxygen flow rate by measuring a pressure in the cannula supplying the patient's airways with oxygen, the detection of the patient's respiration by measuring a pressure variation in the cannula, and when an oxygen-therapy treatment is detected, transformation of the pressure values into respiratory frequency with the aid of an algorithm.

DETAILED DESCRIPTION OF THE INVENTION

Figure 1:
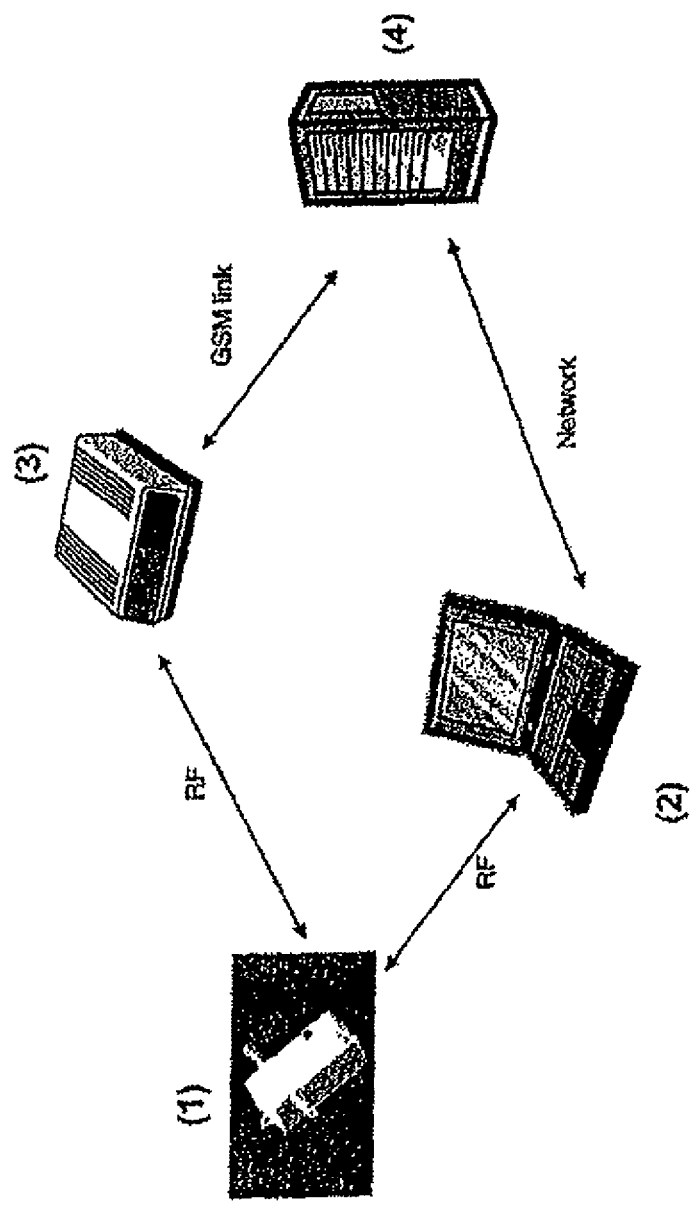
FIG. 1 provides a schematic representation of the modes of possible communication of the device.

The present provides a solution in that the invention is a device intended for the implementation of a system allowing the detection with regard to a patient, of the observance of an oxygen-therapy treatment with an oxygen feed, allowing the recording of the data of said treatment and allowing the transmission of said data.

Accordingly, the device of the invention comprises:
two sensors of absolute pressure, one for measuring the pressure in the cannula serving to deliver the oxygen to the patient's airways, in particular to the nasal pathways, the other for measuring the atmospheric pressure, or a differential pressure sensor;
a micro-processor implementing an algorithm capable of transforming the pressure measurements into respiratory frequencies of the patient and of deducing therefrom the duration of the daily treatment;
a memory chip making it possible to record these data;
a radiofrequency antenna making it possible to ensure the wireless transmission of the data;
a battery allowing the system to operate in complete autonomy, preferably for at least 1 year, preferably still 2 years and more preferably still for at least 3 years.

It is preferable that the oxygen feed occur continuously, nonetheless with an adaptation of the algorithm, the device can also accommodate a discontinuous feed, that is to say solely during the patient's inhalations.

According to one embodiment, the device is located between the nasal cannula of the patient and the oxygen source and it is adaptable to the use of standard cannulas which are not designed specifically for use with said device. Such cannulas comply with the standard NF EN 13544-2 ("*Respiratory Therapy Equipment—Part 2: Tubing and Connectors*") and exhibit only an end-piece for connection to the oxygen source, such as for example the Intersurgical™, Salter™ and Octurno Medizintechnick™ cannulas.

According to another embodiment, the device may be tailored for oxygen sources conventionally used in oxygen-therapy, chosen from among a compressed oxygen cylinder, an oxygen concentrator and a liquid oxygen reservoir. Preferably, the oxygen flow rate is between 0.5 and 4 l/minute. Of course, this flow rate is tailored to the medical prescription.

The device of the invention has a volume and a weight that are low enough for it to be wearable by the patient without pulling on the nasal cannula linking the oxygen source to the patient. Advantageously, the weight of the device is between 20 and 100 g, preferably between 25 and 80 g and more preferably still between about 30 and 50 g.

The device can optionally be worn from the waist by virtue of a suitable fastening system or from the neck by virtue of a pendant-style fastening system.

The device according to the invention can communicate the data recorded by radiofrequency to an office computer or portable computer, a personal digital assistant (PDA) or another apparatus capable of directly recording the transmitted data, or to a GSM modem which will remotely dispatch one or more messages, such as SMSs or the like, containing the recordings of the device, to a care center.

The device uses a radiofrequency in the ISM ("Industrial Scientific Medical") frequency bands which are free for communication and lying between 800 MHz and 5 GHz, preferably between 850 MHz and 3 GHz, still more preferably 868 MHz or 2.4 GHz.

The subject of the invention is also the use of a device according to the invention for tracking the observance of an oxygen-therapy treatment by measuring the duration of treatment of the patient and his respiratory frequency.

The subject of the invention is also a method for tracking the observance of an oxygen-therapy treatment by measuring the duration of treatment of the patient, characterized in that it comprises the following steps:
detection of an oxygen flow rate by measuring a pressure in the cannula,
detection of the patient's respiration by measuring a pressure variation in the cannula, and
when an oxygen-therapy treatment is detected, the transformation of the pressure values into respiratory frequency with the aid of an algorithm.

The objective of this method is to detect by virtue of at least two sensors, on the one hand, the mean overpressure in the cannula due to the oxygen flow rate, and on the other hand the pressure variations related to the inhalations (underpressure) and exhalation (overpressure) of the patient in the cannula, the respiratory frequency being deduced from the pressure variations related to the patient's inhalations/exhalations.

The transformation of the pressure values into respiratory frequency is done with the aid of an algorithm termed "FFT" or of an algorithm termed "TDS". The algorithm is such that it makes it possible to filter the interferences caused by the oxygen sources.

Generally, if a treatment is detected, then to evaluate the respiratory frequency, the algorithms use the pressure values measured periodically over a determined duration, that is to say they use a measurement window comprising a fixed number of samples.

The principle of use of the FFT algorithm is as follows. The Fourier Transform analysis method is applied to the signals received in the measurement window. Certain signals of frequencies are thereafter filtered, such as the signals of frequencies typical of oxygen sources and in particular of oxygen concentrators as well as the signals of lowest and highest frequencies not corresponding to signals of respiratory frequencies. Finally, the frequency resulting from the Fourier Transform analysis which has the highest spectral power will be considered to be the actual respiratory frequency. Generally, to obtain good results, this type of algorithm requires the recording of the spectrum of frequencies for each oxygen source. Only, this step is not generally necessary if the frequencies under the minimum threshold and above the maximum threshold of the respiratory frequency are not taken into account when calculating the respiratory frequency. For greater simplicity (no information is required as regards the oxygen source) and the quality of the results, it is therefore recommended that the spectral powers at these frequencies not be taken into account when using this type of algorithm and in particular when using multiple oxygen sources.

The principle of use of the TDS algorithm for its part is to detect the time at which the pressure signal filtered to eliminate the frequencies due to the oxygen sources crosses an upper threshold signal and a lower threshold signal, the lower and upper threshold signals being constructed on the basis of the mean and standard deviation of the latest data of the filtered-pressure signal. When the signal crosses the upper threshold, the algorithm records this event as being "high". Subsequently, when the signal originates from an upper threshold and crosses the lower threshold, the algorithm records this event as being "low". It again records an event as being "high" when the signal originates from a lower threshold and crosses the upper threshold. The instantaneous respiratory period is the count of the samples between these two "high" events. Once the parameters have been chosen and optimized on the respiratory rhythms of healthy subjects, this algorithm gives results similar to those of FFT. It may turn out to be advantageous to use this algorithm since it is easier to implement than the FFT algorithm and demands less energy during calculation, thereby promoting greater autonomy of the device.

According to the method of the invention, the data regarding the pressure in the cannula are measured during first successive periods $t_1$ with a very low energy consumption, these data measured during said first periods $t_1$ are utilized by said algorithm during second periods $t_2$ during which no other additional pressure datum is recorded, these second periods $t_2$ requiring consumption of energy for the calculation serving to transform the pressure values into respiratory frequency, and with $t_2$ which is a multiple of $t_1$.

The measurement period $t_1$ lies between 20 seconds and 120 seconds and preferably around 60 seconds.

Other aspects, subjects, advantages and characteristics of the invention will be presented on reading the non-restrictive description which follows and which describes preferred embodiments of the invention given by way of examples with reference to the figures.

FIG. 1 illustrates the modes of possible communication of the device according to the invention. The device (1) can transmit by radiofrequency (RF) the data recorded to a personal computer, a personal digital assistant or other apparatus capable of directly recording the transmitted data (2), or to a GSM modem (3), the data recorded by (2) and by (3) subsequently being dispatched up to the care center (4).

Figure 2:
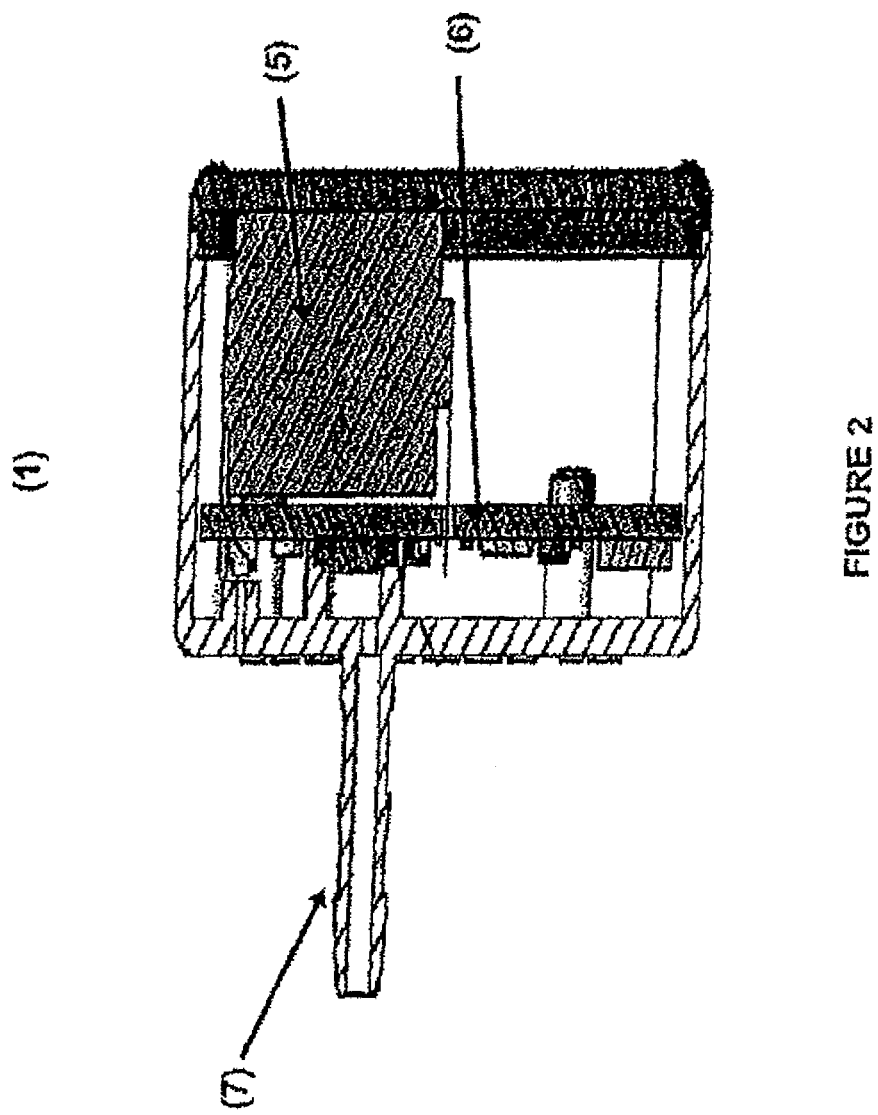
FIG. 2 provides a schematic representation of the device comprising an end-piece and more particularly of the internal cavity of said device.

FIG. 2, for its part, illustrates the interior cavity of the device according to the invention (1) which comprises, inter alia, a battery (5) and a microprocessor (6). The presence of a single end-piece (7) can also be observed in this figure.

Figure 3B:
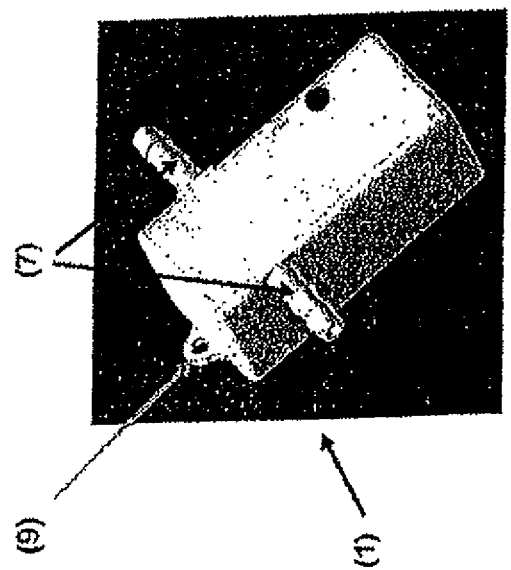
FIG. 3B provides a schematic representation of the device comprising two end-pieces and a pendant-style fastening system.
Figure 3A:
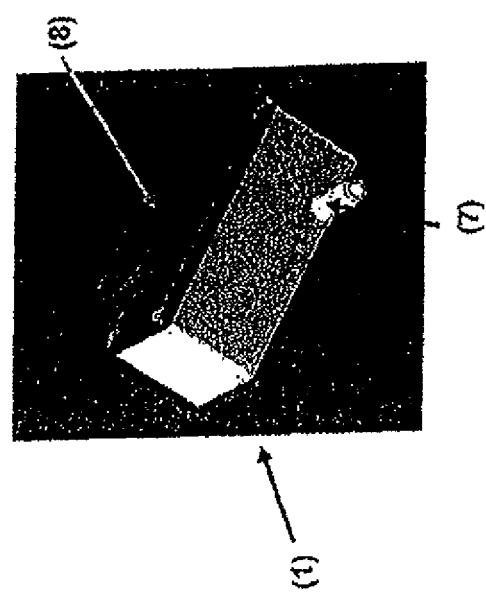
FIG. 3A provides a schematic representation of the device comprising a system for fastening to the waist.

FIG. 3A illustrates the device according to the invention comprising a system for fastening to the waist (8). FIG. 3B illustrates a second embodiment of said device comprising two end-pieces (7) with a pendant-style fastening device (9). It is understood that the fastening systems may equally well be found on the device with one end-piece as that with two end-pieces.

Figure 4:
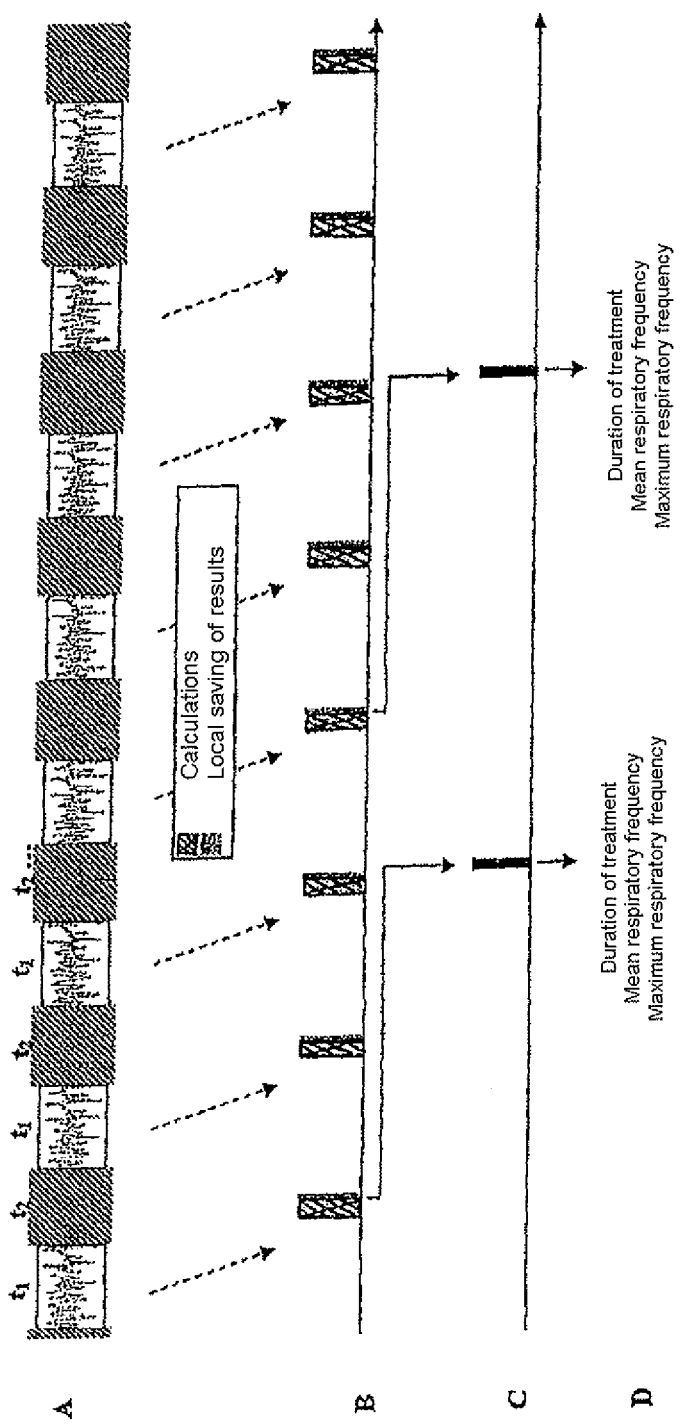
FIG. 4 provides a chart of the steps included in the method for tracking the observance of an oxygen-therapy treatment.

FIG. 4 illustrates the various steps for tracking the observance of an oxygen-therapy treatment.

In (A), the data regarding the pressure in the cannula are measured during successive periods $t_1$. The periods $t_1$ are intercut by periods $t_2$, during which the measured pressure data are utilized by an algorithm.

During these periods $t_2$, no other additional pressure datum is recorded. The algorithm serves to transform the pressure values into respiratory frequency and to detect the following of the treatment, this being translated schematically in B) by a results calculation part and a save part.

In C) when several samples are obtained, there is evaluation of the treatment time for the mean and maximum respiratory frequency.

Finally in D), the duration of the treatment, the mean respiratory frequency and the maximum respiratory frequency are transmitted, for example by radio.

EXAMPLE

The pressure in the cannula is measured successively throughout the duration of the treatment by sensors for a period $t_1$ of 60s called the "measurement window".

Subsequent to this logging of data, the data are utilized during a period $t_2$ during which no additional pressure datum must be recorded.

Between two measurement windows there therefore exists a time period $t_2$ during which the pressure is not recorded. It has been chosen that $t_2$ is a multiple of $t_1$ so as to leave a minimum time period between two windows as well as a time period for the utilization of the data.

The period between the start of one measurement window and the start of the following window is called the "period between two windows" and has a duration equal to a multiple ≥2 of the duration of the measurement window (60s). In each of these periods the pressure signal over 60s is acquired and then it is necessary to determine whether there is treatment over the measurement window and in this case to calculate the corresponding respiratory frequency.

Finally, the results obtained are accumulated over each of the windows for a determined number of periods between 2 measurement windows (≥1); the set of these periods is called the "period for yielding the results".

Over this period, the calculation of the treatment time (sum of the duration of the periods between 2 windows for which a treatment has been observed) is done together with the calculation of the mean and maximum respiratory frequency (mean and maximum of the respiratory frequencies calculated over each period between 2 measurements).

Thus, one may be informed of the state of the patient as regards the observance of his oxygen-therapy treatment and of his respiratory frequency.

Generally, for diseases which may be treated by oxygen-therapy, the device yields the possibility of future studies on the effectiveness of these treatments and of the programs associated with them, and makes it possible to considerably improve the quality and the safety of home care especially by virtue of systems of alerts.

Within this context, the device of the invention appears to be truly innovative since it may be worn continuously by patients in their home, by virtue of its advanced integration— small size, low weight, high autonomy and its adaptability to various oxygen sources, and makes it possible to measure and communicate, remotely, the information relating to the observance of their oxygen-therapy treatment, in particular the duration of effective treatment whatever the source.

Moreover, it makes it possible to measure and transmit the respiratory frequency of these patients, a parameter which could turn out to be very significant in the prevention of exacerbations, i.e. deterioration of the patient's clinical parameters, often giving rise to hospitalization, and which is a source of deterioration of the patient's quality of life.

To sum up, this device allows tracking and safety in home autonomy never before achieved, by virtue of the possibility of alarming the patient and his care center should the prescription not be followed, so as to avoid expensive hospitalization.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for tracking the observance of an oxygen-therapy treatment by measuring the duration of treatment of the patient, wherein the method comprises the steps of:
   a) providing a device for detecting the observance of an oxygen-therapy treatment with feeding of oxygen to a patient via a cannula delivering oxygen to the airways of the patient, the device allowing the recording of the data of the treatment and the transmission of the data, the device comprising two sensors of absolute pressure, one for measuring the pressure in the cannula, the other for measuring the atmospheric pressure, or a differential pressure sensor; a micro-processor implementing an algorithm capable of transforming the pressure measurements into respiratory frequencies of the patient and of deducing therefrom the duration of the daily oxygen-therapy treatment; a memory chip making it possible to record the data; a radiofrequency antenna making it possible to ensure the wireless transmission of the data; and a battery allowing the system to operate in complete autonomy;

b) detecting an oxygen flow rate by measuring a pressure in the cannula supplying the patient's airways with oxygen, c) detecting the patient's respiration by measuring a pressure variation in the cannula, and d) when an oxygen-therapy treatment is detected, transforming the pressure values into respiratory frequency data with the aid of an algorithm and transmitting the respiratory frequency data with the radiofrequency antenna, wherein the method further comprises a step of determining a time period $t_1$, wherein the data regarding the pressure in the cannula are measured during a first plurality of successive daily oxygen-therapy treatment periods ($t_1$), the data measured during said first plurality of daily oxygen-therapy treatment periods ($t_1$) are utilized by said algorithm during a second plurality of daily oxygen-therapy treatment period ($t_2$) during which no other additional pressure datum is recorded, the second plurality of daily oxygen-therapy treatment periods ($t_2$) requiring consumption of energy for the calculation serving to transform the pressure values into respiratory frequency, and wherein $t_2$ is a multiple of $t_1$ and wherein each of the first plurality of successive daily oxygen-therapy treatment periods ($t_1$) is followed in sequence by one of the second daily oxygen-therapy treatment periods ($t_2$).

2. The method of claim 1, wherein the transformation of the pressure values into respiratory frequency is done with the aid of an FFT algorithm or of a TDS algorithm.

3. The method of claim 1, wherein the algorithm is designed to filter the interferences caused by the oxygen sources.

4. The method of claim 1, wherein the measurement period ($t_1$) lies between 20 and 120 seconds.

5. The method of claim 2, wherein the algorithm is designed to filter the interferences caused by the oxygen sources.

6. The method of claim 5, wherein the measurement period ($t_1$) lies between 20 and 120 seconds.

* * * * *